United States Patent
Bae et al.

(10) Patent No.: US 11,517,764 B2
(45) Date of Patent: Dec. 6, 2022

(54) LIGHT IRRADIATION DEVICE FOR SYNTHESIS OF FUNCTIONAL SUBSTANCE IN A HUMAN BODY

(71) Applicant: SEOUL VIOSYS CO., LTD., Ansan-si (KR)

(72) Inventors: Hee Ho Bae, Ansan-si (KR); Yeong Min Yoon, Ansan-si (KR); A Young Lee, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 0 days.

(21) Appl. No.: 16/698,087

(22) Filed: Nov. 27, 2019

(65) Prior Publication Data

US 2020/0171321 A1   Jun. 4, 2020

Related U.S. Application Data

(60) Provisional application No. 62/826,004, filed on Mar. 29, 2019, provisional application No. 62/773,333, filed on Nov. 30, 2018.

(51) Int. Cl.
*A61N 5/06*   (2006.01)

(52) U.S. Cl.
CPC .......... *A61N 5/0613* (2013.01); *A61N 5/0624* (2013.01); *A61N 2005/0626* (2013.01); *A61N 2005/0642* (2013.01); *A61N 2005/0659* (2013.01); *A61N 2005/0661* (2013.01); *A61N 2005/0662* (2013.01); *A61N 2005/0663* (2013.01)

(58) Field of Classification Search
CPC ................ A61N 5/0613; A61N 5/0624; A61N 2005/0662; A61N 2005/0659; A61N 2005/0626; A61N 2005/0642; A61N 2005/0663; A61N 2005/0661; A61N 5/0618; A61N 2005/0627; A61N 2005/0658
See application file for complete search history.

(56) References Cited

U.S. PATENT DOCUMENTS

2007/0188427 A1*  8/2007  Lys .................. H05B 45/46
                                              345/82
2008/0103560 A1*  5/2008  Powell .............. A61N 5/0616
                                              607/88
(Continued)

FOREIGN PATENT DOCUMENTS

EP        3320952     5/2018
JP        11-003616   1/1999
(Continued)

OTHER PUBLICATIONS

Extended European Search Report dated Jul. 14, 2022, for European Patent Application No. 19890616.6.

*Primary Examiner* — Joseph M Dietrich
*Assistant Examiner* — Michael T. Holtzclaw
(74) *Attorney, Agent, or Firm* — H.C. Park & Associates, PLC

(57) ABSTRACT

A light irradiation device includes a first light source emitting first light in a visible wavelength band and a second light source emitting second light, in which at least part of a wavelength band is different from a wavelength band of the first light source and which catalyzes synthesis of a functional substance in a target to which light is applied. The second light includes light in a wavelength band of ultraviolet B.

20 Claims, 12 Drawing Sheets

(56) References Cited

U.S. PATENT DOCUMENTS

| | | | |
|---|---|---|---|
| 2011/0037844 A1* | 2/2011 | Johnson | A61N 5/0613 |
| | | | 348/77 |
| 2014/0121732 A1* | 5/2014 | Goren | A61N 5/0616 |
| | | | 607/95 |
| 2016/0089548 A1* | 3/2016 | Kaas | A01K 29/00 |
| | | | 607/94 |
| 2016/0279439 A1 | 9/2016 | Ferolito | |
| 2016/0303395 A1* | 10/2016 | Moffat | A61N 5/0613 |
| 2017/0080246 A1 | 3/2017 | Knight | |
| 2018/0139817 A1* | 5/2018 | Yamakawa | H01L 33/54 |
| 2018/0318599 A1* | 11/2018 | Van Bommel | H05B 47/155 |
| 2018/0353770 A1* | 12/2018 | Moffat | A61N 5/0616 |
| 2019/0308032 A1* | 10/2019 | Yu | A61N 5/0616 |

FOREIGN PATENT DOCUMENTS

| | | |
|---|---|---|
| KR | 10-2013-0125436 | 11/2013 |
| KR | 10-2014-0141290 | 12/2014 |
| KR | 10-1581441 | 12/2015 |
| KR | 10-2017-0080118 | 7/2017 |
| KR | 10-1910606 | 10/2018 |

\* cited by examiner

LIGHT IRRADIATION DEVICE FOR SYNTHESIS OF FUNCTIONAL SUBSTANCE IN A HUMAN BODY

CROSS-REFERENCE TO RELATED APPLICATIONS

This application claims the benefit of U.S. Provisional Application No. 62/773,333, filed on Nov. 30, 2018, and U.S. Provisional Application No. 62/826,004, filed on Mar. 29, 2019, each of which is hereby incorporated by reference for all purposes as if fully set forth herein.

BACKGROUND

Field

Exemplary embodiments of the invention are directed to a light irradiation device for synthesis of a functional substance in a human body.

Discussion of the Background

In a modern society, people generally spend more time in indoors than outdoors. Accordingly, people are not typically exposed to sufficient sunlight. Sunlight includes light in the ultraviolet wavelength band and light in the infrared wavelength band as well as in the visible wavelength band. Light in each wavelength band of sunlight may have various effects, such as good or bad effects on the human body. As such, there are needs to develop the light irradiation device, which has a spectrum similar to sunlight while providing various functions in a risk-free manner.

However, most light irradiation devices generally have a wavelength band different from that of sunlight, and may be mostly used only as devices for illuminating a dark place. Meanwhile, special light sources providing specific functions are being developed. However, such special light sources are used only as treatment devices.

The above information disclosed in this Background section is only for understanding of the background of the inventive concepts, and, therefore, it may contain information that does not constitute prior art.

SUMMARY

Exemplary embodiments provide a light irradiation device for catalyzing synthesis of a functional substance in a human body.

Additional features of the inventive concepts will be set forth in the description which follows, and in part will be apparent from the description, or may be learned by practice of the inventive concepts.

A light irradiation device according to an exemplary embodiment includes a first light source emitting first light in a visible wavelength band and a second light source emitting second light, in which at least part of a wavelength band is different from a wavelength band of the first light source to catalyze synthesis of a functional substance in a target irradiated with the second light, in which the second light includes light in a wavelength band of ultraviolet B.

The second light may include light in a wavelength band of about 280 nm to about 315 nm.

The second light may further include light in a wavelength band of ultraviolet A and light in a wavelength band of ultraviolet C.

The second light source may emit the second light in a predetermined dose that is harmless to a human body.

The predetermined dose of the second light may be about 30 J/m² to about 10000 J/m².

The predetermined dose of the second light may vary depending on a timing of a day or a year, and an amount of light of the second light source may be controlled depending on the predetermined dose.

The predetermined dose of the second light may vary depending on a location of a human body, and an amount of light of the second light source may be controlled depending on the predetermined dose.

The first light has a wavelength band of about 380 nm to about 780 nm and a spectrum thereof overlaps about 55% or more of an area of a normalized solar spectrum having a color temperature in a range of about 2600 K to about 7000 K.

The normalized solar spectrum is expressed by following Equation 1, Equation 1:

$$E(\lambda, T) = \frac{2hc^2}{\lambda^5} \cdot \frac{1}{e^{hc/\lambda KT} - 1}$$

λ: wavelength (μm)
h: Planck's constant
c: Speed of light
T: Absolute temperature
k: Boltzmann constant.

The light irradiation device may further include a sensing sensor sensing a human body.

The light irradiation device may further include a controller controlling an on/off of each of the first and second light sources depending on whether the human body is present, and a driving unit controlling a light emission direction of at least one of the first and second light sources.

The sensor may sense a movement of the human body, and the driving unit may change the light emission direction of each of the first light source and second light source depending on whether the human body has moved.

The light irradiation device may further include a light source substrate on which the first and second light sources are mounted, and a tilt member provided on the light source substrate and adjusting an angle at which the light source substrate is inclined.

The light source substrate, the first and second light sources may be provided in plural, and the tilt member may be provided on the respective light source substrates and is driven independently.

The light irradiation device may further include one or more switches configured to control an on/off of at least one of the first light source and second light sources.

The on/off of at least one of the first light source and second light sources may be controlled by a user, or the on/off of at least one of the first light source and second light sources may be controlled depending on a predetermined program.

A light irradiation device according to another exemplary embodiment includes a light source emitting light, a location information receiver receiving location information, and a controller receiving the location information from the location information receiver and controlling a dose of light emitted from the light source, in which the controller calculates the dose of light to be emitted from the light source based on the location information and controls the light source to emit light of the calculated dose.

The controller may calculate an appropriate dose based on the location information provided from the location information receiver and controls the light source to emit the appropriate dose.

The location information receiver may calculate the location information of the light irradiation device and the controller may receive the location information to calculate a dose of an external light of a place where the light irradiation device is located, and controls the light source to emit light corresponding to a difference between the appropriate dose and the dose of the external light.

The controller may calculate time information from the location information and control the dose of light depending on the time information.

When a dose which is applied within a range harmless to a human body per day is called an allowable dose, the controller may control the light source to emit light having a dose below the allowable dose.

The light source may include a plurality of light sources emitting light having different wavelength bands.

The light source may include a first light source emitting a first light in a visible light wavelength band and a second light source emitting a second light having a wavelength band different from the wavelength band of the first light. The second light may have an ultraviolet wavelength band. The controller may control the second light source to emit light having a dose lower than a maximum allowable dose of the second light. The second light may have a wavelength band of about 240 nm to about 280 nm.

The first light may have a wavelength band of about 380 nm to 780 nm, and have a spectrum that overlaps about 55% or more of an area of a normalized solar spectrum having a color temperature in a range of about 2,600K to about 7,000K.

The first light may have a wavelength band of about 400 nm to about 500 nm.

The second light may have red to near infrared wavelength bands. The second light may have a wavelength band of about 610 nm to about 940 nm.

The light source may include a first light source emitting a first light of a visible wavelength band, a second light source emitting a second light of an ultraviolet wavelength band, and a third light source emitting a third light of an infrared wavelength band.

The controller may mix and irradiate at least two of the first to third lights.

The light source may be provided in plural, and the light sources may be driven independently.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
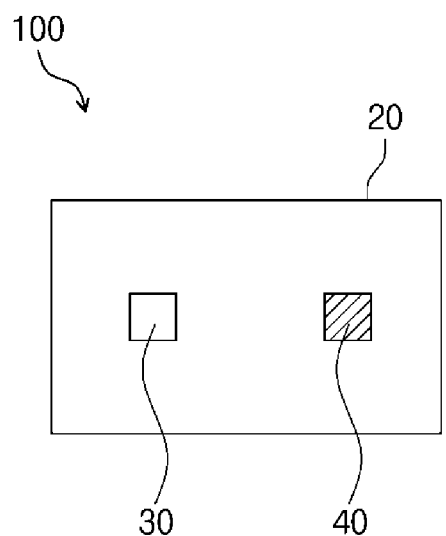
FIG. 1 is a plan view illustrating a light irradiation device according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 is a plan view illustrating a light irradiation device according to an exemplary embodiment.

According to an exemplary embodiment, a light irradiation device 100 includes a first light source 30 emitting first light, a second light source 40 emitting second light, and a light source substrate 20 on which the first and second light sources 30 and 40 are mounted.

The light irradiation device 100 according to an exemplary embodiment may be used as a light irradiation device, as a respective light source capable of implementing the spectrum distribution in a specific wavelength band. To this end, the first light source 30 may emit light in the visible wavelength band. Moreover, the light irradiation device according to an exemplary embodiment may be used as a light source that provides light that catalyzes the synthesis of functional substances, such that the human body may synthesize the predetermined functional substances when light is applied to the human body. To this end, the second light source 40 emits light in a wavelength band, such as the ultraviolet wavelength band, in which the synthesis of functional substances is catalyzed in the human body. In other words, the first light from the first light source includes light in the visible wavelength band, and the second light from the second light source includes light in the ultraviolet wavelength band. As used herein, the wavelength band of the first light is at least partly different from the wavelength band of the second light.

The first light source 30 and the second light source 40 are mounted on the light source substrate 20. As long as the first and second light sources 30 and 40 may be mounted on the light source substrate 20, the light source substrate 20 is not particularly limited and may be provided in various forms. The light source substrate 20 may include a wire to provide power to the first and second light sources 30 and 40. For example, the light source substrate 20 may be formed of a metal board, a printed circuit board, or the like, on which a wire is formed.

The first light source 30 and the second light source 40 may be driven simultaneously or separately. That is, the first and second light sources 30 and 40 may be turned on/off at the same time, or each of the first light source 30 and the second light source 40 may be turned on/off separately. Furthermore, light emitted from the first light source 30 and the second light source 40, e.g., the intensity of each of the first light source 30 and the second light source 40, may be controlled simultaneously or separately.

In an exemplary embodiment, the first light source 30 emits light in the visible wavelength band, and thus, the first light source 30 may be used as a light irradiation device illuminating a predetermined space. For example, the first light source 30 may be a light emitting diode, a fluorescent lamp, or the like, that emits light in the visible wavelength band. However, the type of the first light source 30 is not limited thereto.

Figure 2:
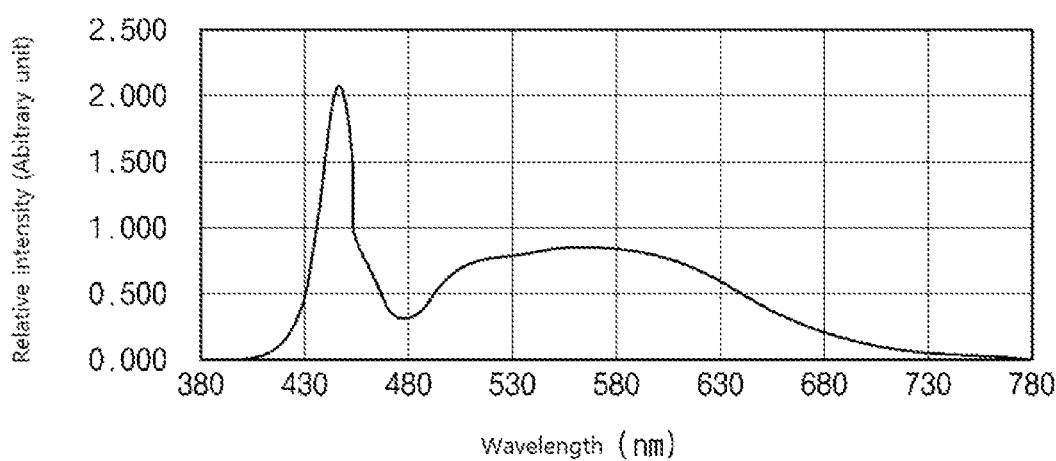
FIG. 2 illustrates a spectrum of first light emitted from a first light source according to an exemplary embodiment.

FIG. 2 illustrates a spectrum of first light emitted from a first light source in a light irradiation device according to an exemplary embodiment. In FIG. 2, the x-axis is a wavelength (nm) and the y-axis is relative intensity. In FIG. 2, the light emitting diode is exemplarily described as emitting light in the visible wavelength band.

Referring to FIG. 2, the first light source emits light in the wavelength range of about 380 nm to about 780 nm, as the first light. The first light source operates as a light irradiation device that illuminates a predetermined area. The first light emitted from the first light source may include light in the ultraviolet or infrared region. However, the intensity of the first light is very weak, and most of the first light is distributed in the visible wavelength band.

In an exemplary embodiment, the second light source emits light that induces and catalyzes the synthesis of specific functional substances in a human body. Light emitted by the second light source, that is, the second light, may include various wavelength bands capable of inducing the synthesis of specific functional substances in the human body. For example, the second light may be ultraviolet light, visible light, and/or infrared light. The wavelength band of the second light may partly overlap with the wavelength band of the first light. However, the second light source emits light in a wavelength band that is at least partly different from the wavelength band of the first light.

In an exemplary embodiment, the second light may be in an ultraviolet wavelength band and, in particular, may be in the wavelength band of ultraviolet B of the ultraviolet wavelength band.

In an exemplary embodiment, the target to which light is applied may be an organism, for example, a plant or an animal, which is capable of synthesizing a specific functional substance when the target is exposed to predetermined light. In particular, the target to which light is applied may correspond to a human body. When the human body is exposed to the predetermined ultraviolet light, vitamin D, which is one of the functional substances, may be synthesized in the human body. To this end, the ultraviolet light applied to the human body may be in a wavelength band of ultraviolet B. When the human body is exposed to light in the wavelength band of ultraviolet B, 7-dehydrocholesterol in skin cells synthesizes cholecalciferol (i.e., Vitamin D3).

In an exemplary embodiment, the second light corresponding to ultraviolet B may include light in the wavelength band of about 280 nm to about 315 nm.

However, the wavelength band of the second light is not limited thereto, and in some exemplary embodiments, the second light may include light in the wavelength band of ultraviolet A and/or ultraviolet C in addition to the wavelength band of ultraviolet B.

In general, ultraviolet light is known to have a harmful effect on the human body when a predetermined dose or more is applied to the human body. In the light irradiation device according to an exemplary embodiment, the second light is applied to the human body by the allowable dose or less. As used herein, the allowable dose may refer to a dose in a range that is harmless to the human body when the allowable dose is applied to the human body. For example, the allowable dose of the second light may be about 30 $J/m^2$ to about 10000 $J/m^2$.

As described above, the light irradiation device according to an exemplary embodiment may include a first light source as a general light irradiation device and a second light source for catalyzing the synthesis of the functional substance, thereby catalyzing the synthesis of the functional substance in a human body as well as illuminating a predetermined area as the general light irradiation device.

In an exemplary embodiment, the first light source may be used as various devices in the range capable of being used as a light irradiation device.

Figure 3A:
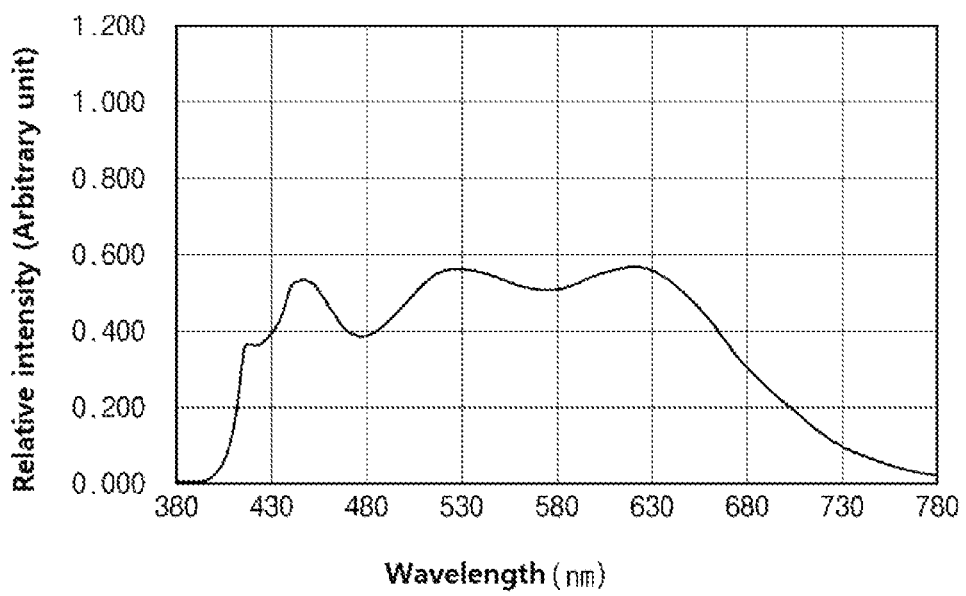
FIG. 3A illustrates spectrum of first light emitted from a first light source according to another exemplary embodiment.

FIG. 3A illustrates a spectrum of first light emitted from a first light source according to another exemplary embodiment. In FIG. 3A, the x-axis is a wavelength (nm) and the y-axis is relative intensity.

Referring to FIG. 3A, the first light source may emit first light having the wavelength band of about 380 nm to about 780 nm. As the first light according to an exemplary embodiment has a similar spectrum to that of sunlight, the first light will be described by comparing the first light with the sunlight.

Figure 3B:
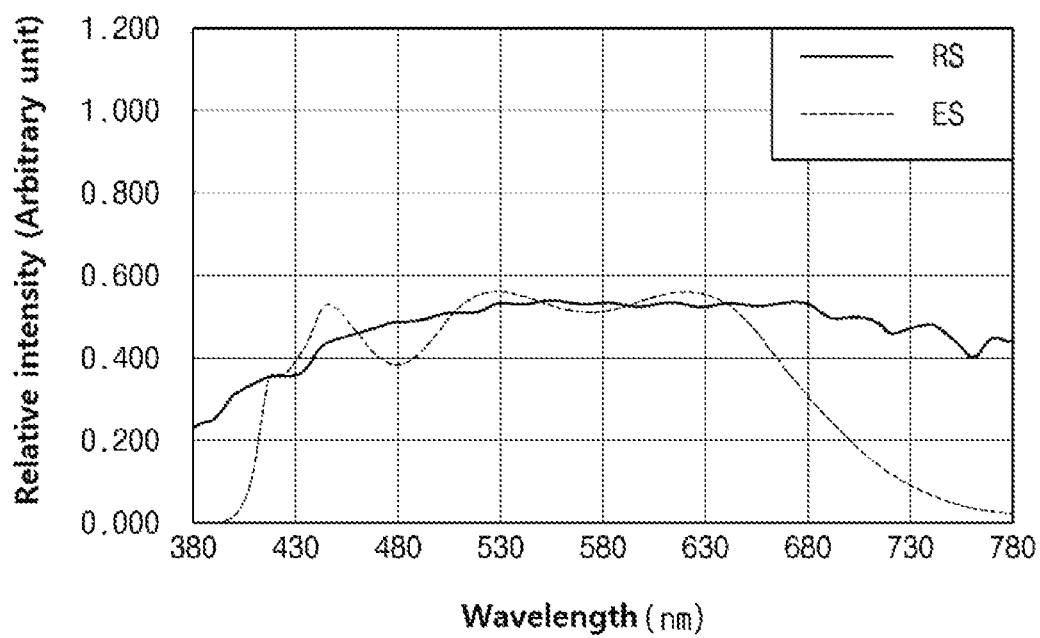
FIG. 3B illustrates spectrum of the first light of FIG. 3A together with solar spectrum.

FIG. 3B illustrates a spectrum of the first light of FIG. 3A together with solar spectrum.

Referring to FIG. 3B, the first light according to an exemplary embodiment may correspond to light having an area that overlaps about 55% or more of an area of the normalized solar spectrum in a range, in which color temperature is from about 2600 K to about 7000 K. In the wavelength band of about 380 nm to about 490 nm, the peak of the first light may have the deviation of 0.14 or less from the normalized solar spectrum.

The normalized solar spectrum may be expressed as the following Equation 1.

[Equation 1]

$$E(\lambda, T) = \frac{2hc^2}{\lambda^5} \cdot \frac{1}{e^{hc/\lambda kT} - 1}$$

λ: wavelength (μm)
h: Planck's constant
c: Speed of light
T: Absolute temperature
k: Boltzmann constant 'RS' denotes solar spectrum, and 'ES' denotes the spectrum of light emitted by a light source according to an exemplary embodiment. The solar spectrum may correspond to the spectrum in which the color temperature is 5000 K.

The first light source according to an exemplary embodiment has a similar spectrum to that of sunlight. However, light emitted from the first light source may be different from sunlight in that the first light source emits light other than most of light in the ultraviolet wavelength band. The light source according to an exemplary embodiment emits light in the wavelength band of about 380 nm to about 780 nm substantially corresponding to the entire wavelength band of the visible light.

The first light source according to an exemplary embodiment emits light corresponding to a part of the wavelength band of the visible light, rather than the entire wavelength band of the visible light. For example, the first light source may emit light in the wavelength band of about 400 nm to about 630 nm.

As used herein, the term "similar to sunlight" may refer that an overlapping area is not less than a predetermined value with respect to the normalized solar spectrum and the deviation of the peak (e.g., the degree deviating from the peak of the solar spectrum) from the solar spectrum is not greater than a predetermined value. For example, in an exemplary embodiment, the light source may emit light having an area that overlaps about 55% or more of an area of the normalized solar spectrum, and the peak of light may have the deviation of about 0.14 or less compared with the normalized solar spectrum.

In addition, sunlight may have various color temperatures depending on a point in time. The light source according to an exemplary embodiment may emit light having the similar spectrum to the spectrum of the sunlight having different color temperatures.

The sunlight may have a variety of therapeutic effects when applied to the human body, in particular, a human eye. For example, frequent exposure to sunlight may lower the prevalence of myopia. An insufficient exposure to sunlight due to low outdoor hours may render the eyeball to grow long, and thus, the eyeball may become oval. Accordingly, myopia may occur. However, the use of a first light source similar to the sunlight according to an exemplary embodiment may reduce the prevalence of myopia.

Furthermore, the first light source may provide light in a wavelength band that is very similar to sunlight, and thus, the side effects caused by excessive blue light may be minimized.

When the conventional light source (e.g., the conventional light emitting diode) is used as the first light source, the intensity of light in the blue wavelength band may be very high due to the characteristics of the conventional light emitting diode as shown in FIG. 2. In addition, the second light source may mainly emit light in the ultraviolet wavelength band. However, light in the blue wavelength band may be also emitted together although the intensity thereof may be low. In this case, light of the blue wavelength band of the second light overlaps with light of the blue wavelength band of the first light source, and thus, the intensity of light in the blue wavelength band is likely to be very large. When eyes are continuously exposed to excessive light in the blue wavelength, the risk of eye disease, such as the macular degeneration and cataract of the eye, may be increased.

However, when the light source according to another exemplary embodiment is used as the first light source, because light in the blue wavelength band does not appear particularly strong as being similar to sunlight, it is possible to irradiate light with proper intensity in the entire wavelength band without excessively irradiating light in the blue wavelength. As such, the side effects due to the excessive exposure to light in the blue wavelength band may be minimized.

Furthermore, when the light source according to an exemplary embodiment is used as the first light source, light in the wavelength band of about 380 nm to about 780 nm is emitted, and thus, light in the ultraviolet wavelength band is not substantially emitted or is emitted in very little amount. As such, when the ultraviolet light is provided using the second light source, it is possible to provide the ultraviolet ray, which is similar to sunlight, in particular, the light of ultraviolet B.

In addition, when the light irradiation device according to an exemplary embodiment is used, it is possible to select the on/off of the second light source that emits light in the ultraviolet wavelength band as well as the first light source emitting the light in the visible wavelength band. For example, one or more switches may be provided to the light irradiation device such that a user may directly manipulate the on/off of the first light source and/or second light source. The switch may be positioned adjacent to the first and/or second light source, or may be disposed spaced from the first and/or second light source. The switch may be electrically and physically connected to the first and/or second light source. However, the inventive concepts are not limited thereto. In some exemplary embodiments, the switch may be wirelessly connected to the first and/or second light source. Also, the switch may have various shapes, so long as the switch is capable of receiving a signal. For example, the switch may have the shape of a general press button, or may be provided as a touch input device using a touch screen.

In addition, a user may also manipulate the on/off of the first and/or second light sources using an automatic program, as well as directly and manually manipulating the on/off of the first and/or second light sources. The user may set the mode in which the driving time, the degree of light emission, or the like of the first and/or second light source is programmed, in advance. The on/off of the first and/or second light source may be automatically controlled without an additional user input, by performing the mode.

When sunlight is applied to the human body, light in the ultraviolet wavelength band may be included. As such, it may be impossible to be selectively exposed to light in the ultraviolet wavelength band. However, in the light irradiation device according to an exemplary embodiment, the user may determine whether to be exposed to light in the ultraviolet wavelength band. As such, a person who needs to synthesize the specific functional substance may turn on the second light source, thereby effectively catalyzing the synthesis of the functional substance.

As such, the light irradiation device according to an exemplary embodiment allows a user to get light very similar to sunlight, regardless of time and place. In addition, the light irradiation device may allow the user to be selectively exposed to light of a specific wavelength, such as ultraviolet light.

The light irradiation device according to an exemplary embodiment may be applied to the room of the hospital that requires the synthesis of a specific functional substance, thereby improving the treatment effect for patients. Also, the light irradiation device according to an exemplary embodiment may be applied to a variety of portable devices, and thus, there is almost no restriction on the place and time. As such, the light irradiation device according to exemplary embodiments provides people who can't get sunlight, for example, people who have been indoors for a long time, people who work at night, or the like, with a variety of effects that may be obtained from sunlight.

The light irradiation device according to an exemplary embodiment may be implemented in various forms.

Figure 4A:
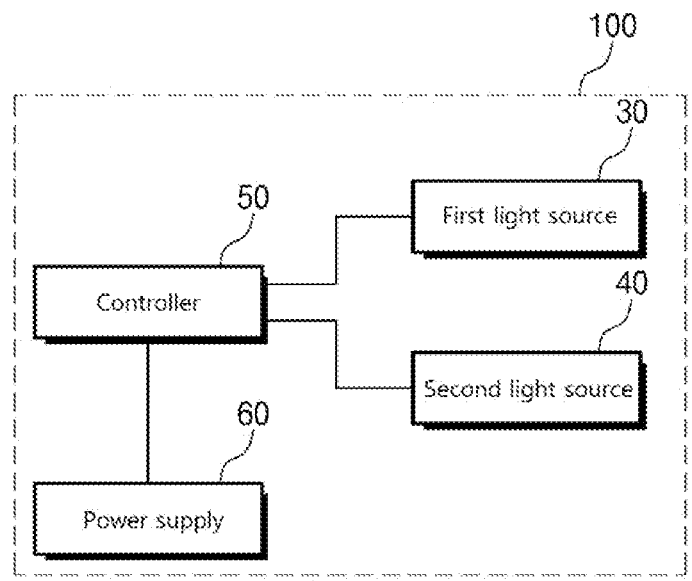
FIGS. 4A, 4B, and 4C are block diagrams illustrating a light irradiation device according to exemplary embodiments
Figure 4B:
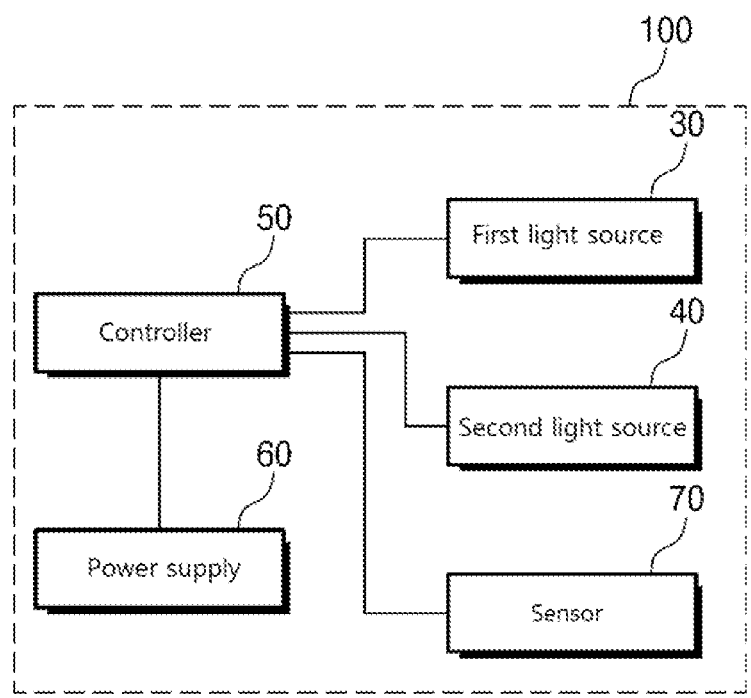
Figure 4C:
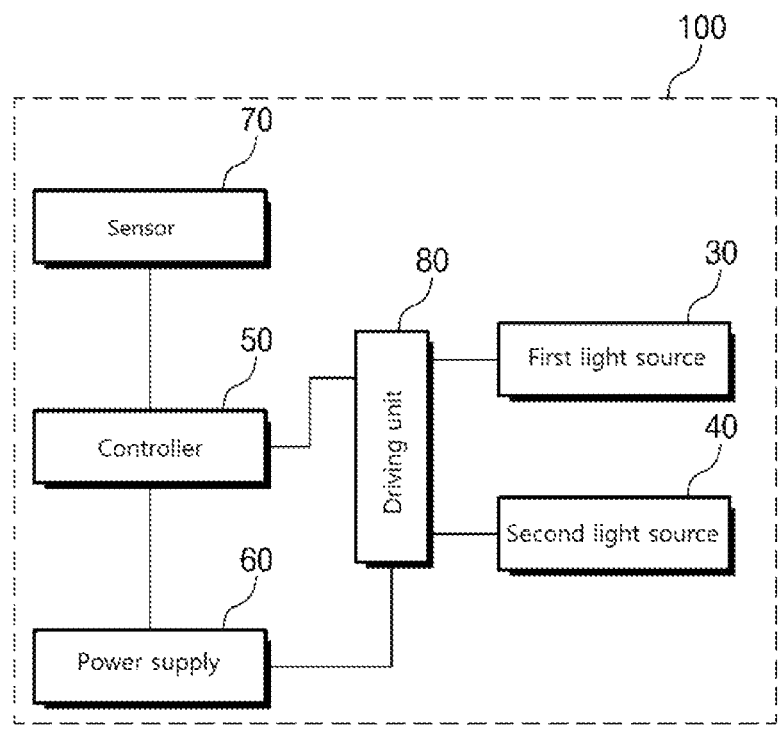

FIGS. 4A to 4C are block diagrams illustrating a light irradiation device according to exemplary embodiments.

Referring to FIG. 4A, the light irradiation device 100 according to an exemplary embodiment may include the first light source 30 emitting first light, the second light source 40 emitting second light, a controller 50 controlling the first and second light sources 30 and 40, and a power supply 60 supplying power to the controller 50 and the first and second light sources 30 and 40.

As described above, each of the first and second light sources 30 and 40 may emit the first light including the visible wavelength band and the second light including the ultraviolet wavelength band.

The controller 50 may control whether to emit light from the first and second light sources 30 and 40, the amount of light, the intensity of light, the emission time of light, or the like. Features of light may be controller by the controller 50 in various manners. For example, the controller 50 may adapt a method of continuously emitting light, a method of sequentially decreasing or increasing the intensity of light, a blinking method, a mixed method, or the like.

One or more switches that allow a user to select the on/off of the first and second light sources 30 and 40 may be connected to the controller 50.

The power supply 60 is electrically connected to the first and second light sources 30 and 40 and the controller 50, so as to supply power to the first and second light sources 30 and 40 and the controller 50. The power supply 60 in FIGS. 4A to 4C is exemplarily illustrated as supplying power to the first and second light sources 30 and 40 through the controller 50. However, the inventive concepts are not limited thereto. For example, in some exemplary embodiments, the power supply 60 is directly connected to the first and second light sources 30 and 40 so as to supply power to the first and second light sources 30 and 40.

The light irradiation device 100 may further include an optical unit that selectively focuses or emits light emitted from the first and second light sources 30 and 40. The optical unit may focus light generated from the first and second light sources 30 and 40 in the narrow or wide range as needed. Alternatively, light may be focused or distributed in the uniform or non-uniform form depending on the location at which light is to be emitted. The optical unit may include at least one or more lenses as needed. The lens may perform various functions of focusing, distributing, uniformizing, non-uniformizing, or the like of light from the first and second light sources 30 and 40.

For example, when light is irradiated in the narrow area by using the light irradiation device 100 according to an exemplary embodiment, the lens for focusing light may be used in the first and second light sources 30 and 40. On the other hand, when light is provided in a wide area, for example, the entire room, using the light irradiation device 100 according to an exemplary embodiment, the lens for distributing light may be used.

Referring to FIG. 4B, the light irradiation device 100 according to another exemplary embodiment may further include a sensor 70 that senses the environment of a place to which light from the light irradiation device 100 is applied, in addition to components illustrated in FIG. 4A. The light irradiation device 100 may be operated in a manual mode or an automatic mode, depending on the result sensed by the sensor 70.

The sensor 70 may sense various factors that affect the driving of the first and second light sources 30 and 40, and may be provided in various forms. For example, the sensor 70 may be a motion sensor that senses the motion of a human body as the sensor 70 that senses whether the human body is present. The human body is usually accompanied by movement, and thus, the presence of the human body may be determined by detecting such the movement. In addition, the sensor 70 may include an illuminance sensor that detects whether external light is present in a place to which light emitted from the light irradiation device is applied, as well as a human body. The controller 50 may turn on or off the first light source 30 and the second light source 40 depending on the sensing result of at least one of the illuminance sensor and/or the motion sensor.

The motion sensor may sense whether the human body is activated. When the activity of a user is sensed by the motion sensor, the first light source 30 and the second light source 40 may be turned on. When the activity of a user is not sensed by the motion sensor, the first light source 30 and the second light source 40 may be turned off. Alternatively, when it is determined through the motion sensor that the distance between a light irradiation device and a user reaches a predetermined distance, the second light source 40 may be turned off.

The illuminance sensor may sense the illuminance of ambient external light. After setting the illuminance range of ambient light to at least one or more, the controller 50 may turn on/off the first and second light sources 30 and 40 depending on the illuminance range of the detected ambient light, or may adjust the amount of light from the first and second light sources 30 and 40. For example, when the illuminance of the ambient external light is high due to sunlight, the controller 50 may lower the illuminance of the first light source 30 and may turn off the second light source 40.

In this manner, the light irradiation device according to an exemplary embodiment may be used in various manners, for example, selectively driving the first and second light sources 30 and 40 depending on whether the human body is active or the amount of external light, thereby reducing power consumption.

Referring to FIG. 4C, in addition to the components illustrated in FIG. 4B, the light irradiation device according to another exemplary embodiment may further include a driving unit 80 that controls the light emission direction of at least one of the first light source 30 and the second light source 40.

After detecting whether the human body is present and whether the human body is moved, based on the sensing information from the above-described sensor 70, the driving unit 80 may change the light emission direction of at least one of the first light source 30 and the second light source 40, such that light is emitted toward the human body or away from the human body.

The shape of the driving unit 80 is not particularly limited as long as the driving unit 80 may adjust the light output location of each of the first and second light sources 30 and 40. For example, the driving unit 80 may be a tilt member, which will be in more detail described later.

FIGS. 4A to 4C exemplarily illustrate the light irradiation device in the form of a block diagram, but the light irradiation device according to exemplary embodiments may be implemented in various forms. Hereinafter, specific exemplary embodiments of the light irradiation device will be described.

Figure 5A:
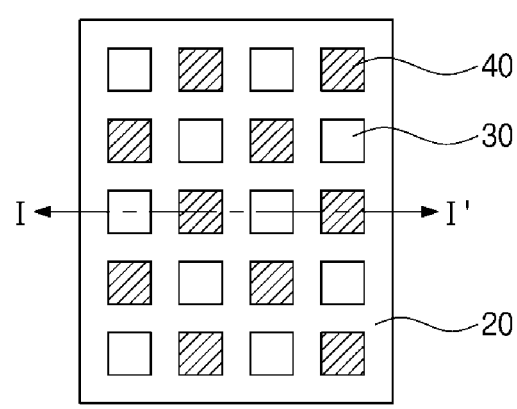
FIG. 5A is a plan view of a light irradiation device according to an exemplary embodiment.
Figure 5B:
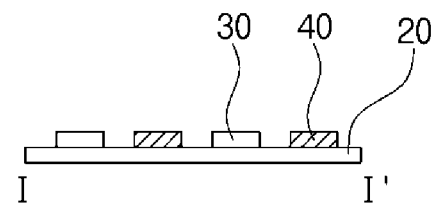
FIG. 5B is a cross-sectional view taken along line I-I' of FIG. 5A.

FIG. 5A is a plan view of a light irradiation device according to an exemplary embodiment, and FIG. 5B is a cross-sectional view taken along line I-I' of FIG. 5A.

Referring to FIGS. 5A and 5B, a light irradiation device according to an exemplary embodiment may include the first light source 30, the second light source 40, and the light source substrate 20, on which the first and second light sources 30 and 40 are mounted.

The first light source 30 according to an exemplary embodiment may be provided as a plurality of parts, and the second light source 40 may also be provided as a plurality of parts. For example, the number of first light sources 30 may be the same as the number of second light sources 40. As illustrated in FIGS. 5A and 5B, the first light sources 30 and the second light sources 40 may be alternately arranged in a matrix form. However, the number of first light sources 30 and the number of second light sources 40 are not limited thereto, and the number of first light sources 30 may be greater or less than the number of second light sources 40 in other exemplary embodiments. Furthermore, the first light sources 30 and the second light sources 40 may be regularly or irregularly arranged depending on the number of first light sources 30 and the number of second light sources 40.

The light irradiation device according to an exemplary embodiment may further include housing for accommodating the first and second light sources 30 and 40 and the light source substrate 20. A transmission window, through which light emitted from the first and second light sources 30 and 40 passes, may be provided in the housing. In this manner, light emitted from the first and second light sources 30 and 40 may be provided to the human body through the transmission window.

In an exemplary embodiment, the controller 50 may be provided on the light source substrate 20 in various forms. For example, the controller 50 may be provided as a separate circuit wire, or as a separate chip mounted on the light source substrate 20.

Figure 6A:
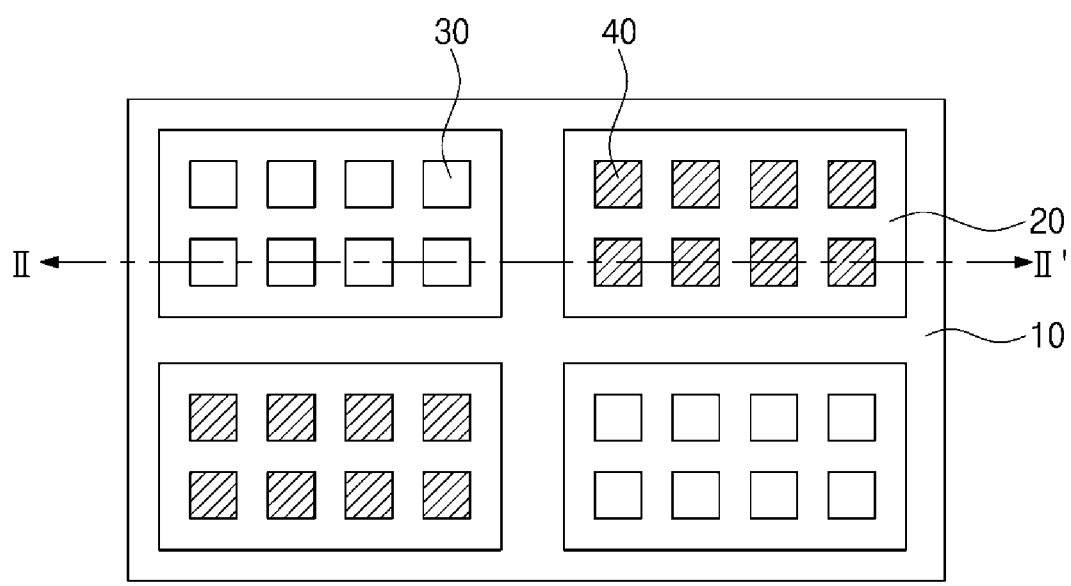
FIG. 6A is a plan view of a light irradiation device according to an exemplary embodiment.
Figure 6B:
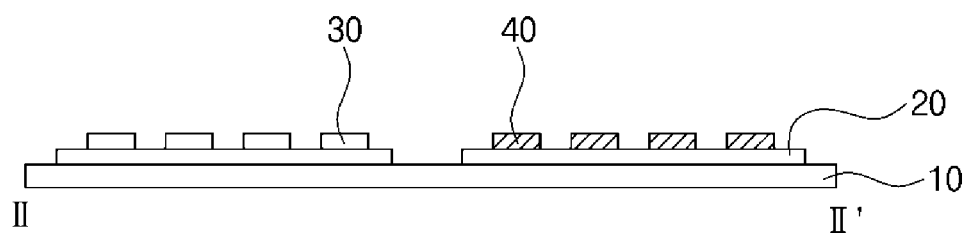
FIG. 6B is a cross-sectional view taken along line II-II' of FIG. 6A.

FIG. 6A is a plan view of a light irradiation device according to an exemplary embodiment, and FIG. 6B is a cross-sectional view taken along line II-IF of FIG. 6A.

Referring to FIGS. 6A and 6B, in addition to the components of the light irradiation device of FIG. 5A described above, a light irradiation device according to the illustrated exemplary embodiment may further include a base substrate 10, on which the light source substrate 20 formed with the first and second light sources 30 and 40 is mounted.

The base substrate 10 may include wirings therein to provide power to the first and second light sources 30 and 40 and/or the light source substrate 20. For example, the base substrate 10 may be formed in various forms, such as a metal board or a printed circuit board, on which wirings are formed.

In an exemplary embodiment, the light source substrate 20 may be provided as a plurality of part. At least one of the first light sources 30, at least one of the second light sources 40, or both the first and second light sources 30 and 40 may be provided on the light source substrates 20. FIG. 6A exemplarily illustrates that the base substrate 10 includes four light source substrates 20, the first light sources 30 are provided on two of the light source substrates 20, and the second light source substrates 20 are provided on the other two of the light source substrates 20. As such, each of the light source substrates 20 may be provided in the form of a package in which a plurality of light sources are mounted. In this case, a light irradiation device may be easily manufactured by forming a plurality of packages on the base substrate 10.

In an exemplary embodiment, the controller may be provided on the at least one light source substrate 20 and the base substrate 10 in various forms. For example, the controller may be formed as a separate circuit wire or a separate chip, which may be mounted on the at least one light source substrate 20 and the base substrate 10.

Figure 7A:
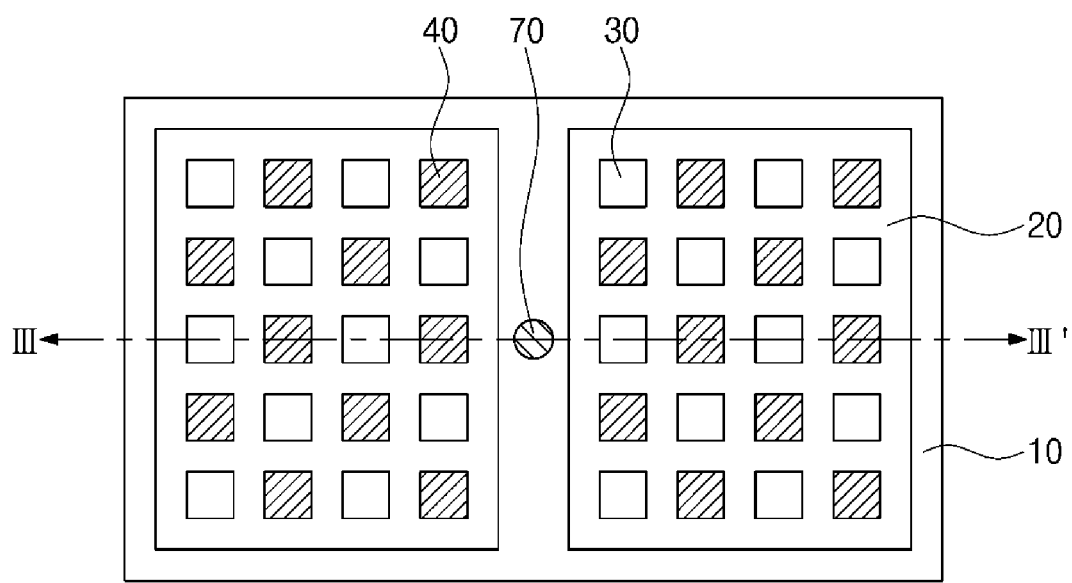
FIG. 7A is a plan view of a light irradiation device according to an exemplary embodiment.
Figure 7B:
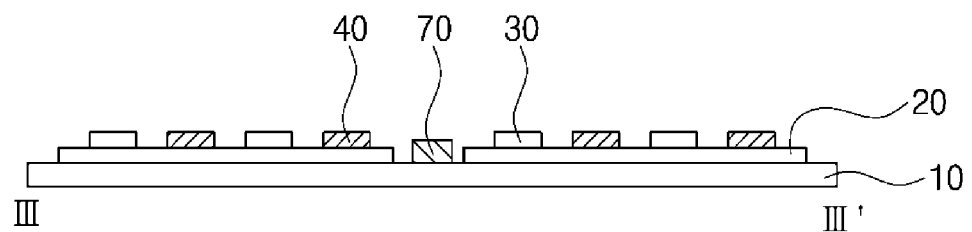
FIG. 7B is a cross-sectional view taken along line III-III' of FIG. 7A.

FIG. 7A is a plan view of a light irradiation device according to an exemplary embodiment, and FIG. 7B is a cross-sectional view taken along line of FIG. 7A.

Referring to FIGS. 7A and 7B, in addition to the components of the light irradiation device of FIG. 6A described above, a light irradiation device according to the illustrated exemplary embodiment may further include the sensor 70.

In an exemplary embodiment, the sensor 70 may be provided on the base substrate 10. However, the location of the sensor 70 is not particularly limited. For example, in some exemplary embodiments, the sensor 70 may be provided on the light source substrate 20, or the sensor 70 may be separately disposed at a location spaced from the base substrate 10 or the light source substrate 20. When the sensor 70 is positioned in a separate location spaced from the base substrate 10 or the light source substrate 20, the sensor 70 and the controller 50 may be connected in a wired or wireless manner.

The sensor 70 may sense various factors that affect the driving of the first and second light sources 30 and 40, and may be provided in various forms. For example, the sensor 70 may be a motion sensor that senses the motion of a human body as a sensor that senses whether the human body is present. Moreover, the sensor 70 may be an illuminance sensor that detects whether external light is present in a place where light emitted from the light irradiation device is to be applied, as well as a human body.

The sensor 70 may further include a rotating member or a vertical moving member capable of adjusting the sensing direction of the sensor 70. The sensor 70 may easily detect the target to be detected using the rotating member or the vertical moving member.

FIG. 7A exemplarily shows that the light irradiating device includes one sensor 70. However, the inventive concepts are not limited thereto, and the sensor 70 may be provided in plural. In this case, the same type of sensors 70 may be provided in plural, or the different sensors 70 may be provided.

Figure 8A:
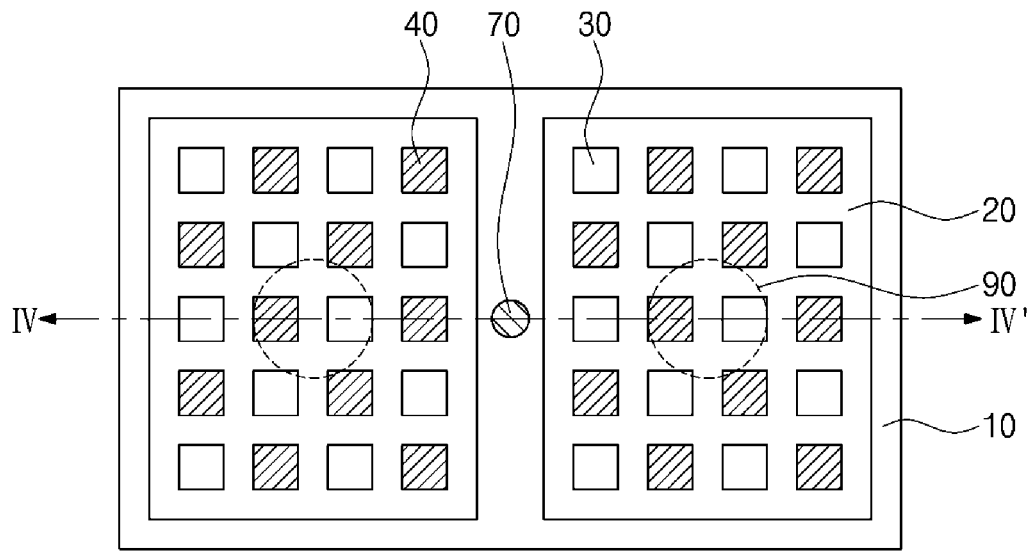
FIG. 8A is a plan view of a light irradiation device according to an exemplary embodiment.
Figure 8B:
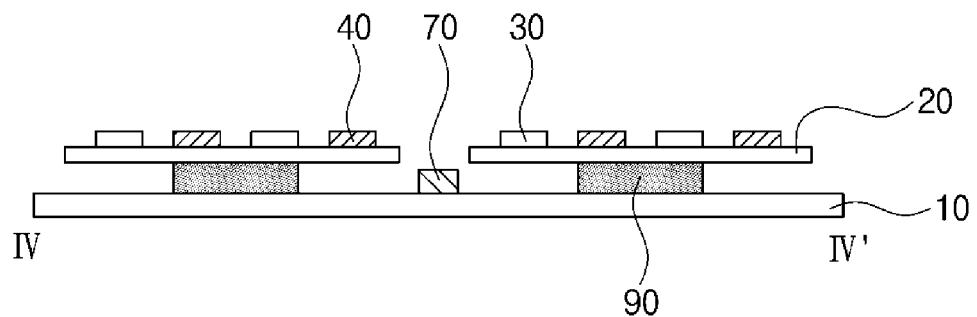
FIG. 8B is a cross-sectional view taken along line IV-IV' of FIG. 8A.

FIG. 8A is a plan view of a light irradiation device according to another exemplary embodiment, and FIG. 8B is a cross-sectional view taken along line IV-IV' of FIG. 8A.

Referring to FIGS. 8A and 8B, in addition to the components of the light irradiation device of FIG. 7A described above, a light irradiation device according to the illustrated exemplary embodiment may further include a driving unit. The driving unit may control the light emission direction of at least one of the first light sources 30 and the second light sources 40.

The driving unit may be provided to each of the first and second light sources 30 and 40, and may individually control the light emission direction of each of the first and second light sources 30 and 40. In some exemplary embodiments, the driving unit may control the slope of the light source substrate 20. For example, a tilt member 90 may be provided as a driving unit between the base substrate 10 and each of the light source substrates 20 when the number of light source substrates 20 is at least two, and the first and second light sources 30 and 40 may be provided on each of the light source substrates 20. The tilt member 90 is provided between the base substrate 10 and the light source substrate 20, and thus, the inclined angle may be adjusted. The tilt member 90 may be provided in various forms and may move the light source substrate 20 in a predetermined direction.

After detecting whether the human body is present and whether the human body is moved based on the sensing information from the above-described sensor 70, the driving unit may change the light emission direction of at least one of the first light source 30 and the second light source 40, such that light is emitted toward the human body or away from the human body.

The controller 50 receives information of the human body from the sensor 70 and controls the on/off of the first and second light sources 30 and 40. At the same time, the controller 50 may change the angle of the light source substrate 20, using the driving unit, such as the tilt member 90, to emit light towards the human body.

Figure 8C:
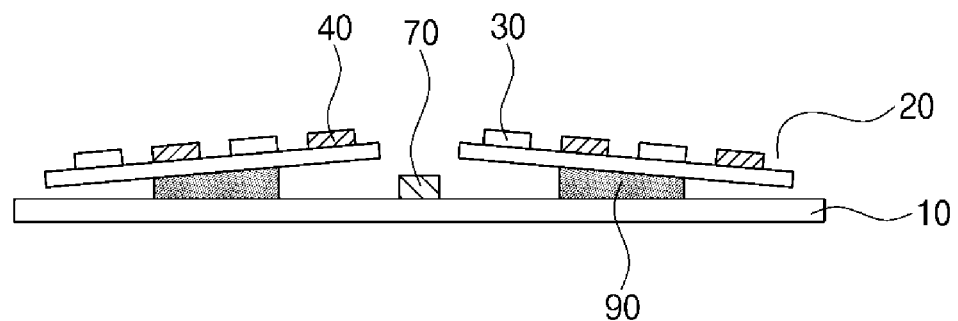
FIG. 8C is a cross-sectional view illustrating a light source substrate inclined by driving a tilt member.

FIG. 8C is a cross-sectional view illustrating the light source substrate 20 inclined by driving the tilt member 90, in the light irradiation device employing the tilt member 90.

The tilt member 90 is provided for each of the light source substrates 20, and may be driven independently. In particular, when two or more driving units are provided, the first and second light sources 30 and 40 connected to each driving unit may be driven individually. Accordingly, it is possible to provide respective light in different directions. For example, when the sensor 70 detects a plurality of human bodies, it is possible to provide respective light irradiation devices according to the movement of the human body.

In addition, even though a plurality of human bodies are not detected, when a specific area is assigned and then a respective light irradiation device needs to be provided to the specific area, a separate light irradiation device may be provided in a plurality of areas. For example, when separate therapeutic light irradiation devices need to be provided in a plurality of areas in the hospital room, the separate therapeutic light irradiation devices may be positioned, such that light is emitted for each of the plurality of areas by including a plurality of driving units, thereby providing light in each area.

As described above, the first and second light sources may be individually controlled by the controller, and thus, the light irradiation device may provide the first light and the second light with various intensities in various directions. In particular, in the light irradiation device according to an exemplary embodiment, light from at least part of the first and second light sources may be provided to the human body by a predetermined dose, instead of sunlight.

Humans are exposed to light in a specific wavelength band in sunlight, and thus, the synthesis of functional substances, such as vitamin D, is catalyzed. As such, the human body needs to be exposed to sunlight to a proper degree to synthesize the predetermined degree of functional substances. However, in the case of sunlight, the wavelength band and intensity thereof changes with time (e.g., what time of day or what day of the year) or depending on a location (e.g., what is latitude or longitude).

Figure 9:
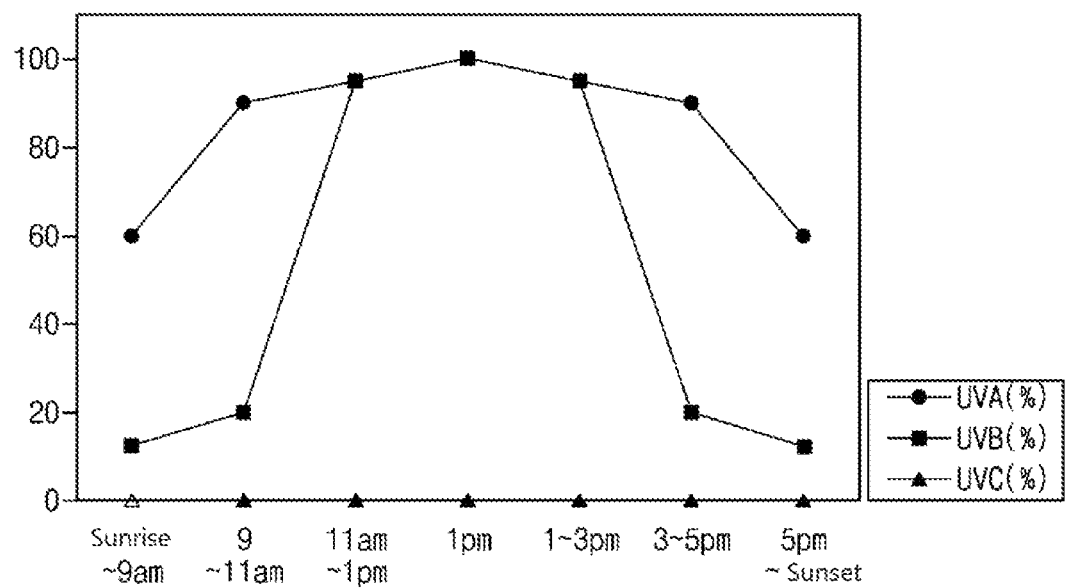
FIG. 9 is a graph illustrating the intensity of ultraviolet light of sunlight with time during a day.

FIG. 9 illustrates the intensity of ultraviolet light of sunlight with time during a day. As illustrated in FIG. 9, in the case of sunlight, the intensity of ultraviolet light continuously varies throughout the day. As such, it is not easy to expose a human body to sunlight to a level of each of the first light and the second light, which is actually required by the human body.

The light irradiation device according to an exemplary embodiment may provide the human body with an appropriate amount of light corresponding to sunlight by controlling the first and second light sources depending on the timing or the location. More particularly, the amount and intensity of light from the first and second light sources, in particular, the amount and intensity of light from the second light source, may be adjusted such that the ultraviolet light of the maximum allowable amount or less is exposed to the human body depending on the location of the sun or depending on the intensity or irradiation time of the ultraviolet light of sunlight. For example, the allowable dose of the second light may be set to a value varying depending on the season, and the second light from the second light source may be controlled depending on the allowable dose.

In the light irradiation device according to an exemplary embodiment, the amount of light and intensity of each of the first light and the second light may be set to various modes. The user may select one of the various modes to receive the first light and the second light depending on the selected mode.

For example, the light irradiation device may be set to the first to fifth modes. The first mode may be a mode of providing only the basic lighting, that is, the mode in which only the first light source is turned on, as the default lighting mode. The second mode may be a mode in which the color temperature and wavelength of each of the first light and the second light are changed depending on the morning, lunch, and dinner time zones, as a dynamic mode. The third mode may be a mode in which the second light source is turned on such that the second light is emitted more as a main light source than the first light, as an artificial light enhancement mode. The fourth mode may be a mode in which the first and second light sources are turned on as most similar to sunlight, as a sunlight mode. The fifth mode may be a mode in which a user selects the on/off of each of the first and second light sources and the amount and intensity of each of the first light and the second light, as a user setting mode.

In this manner, a setting value of the light irradiation device may be easily changed depending on the condition desired by the user.

The light irradiation device according to an exemplary embodiment may be variously applied to a place where the treatment by the lighting and ultraviolet light is required. For example, the light irradiation device may be used for the light irradiation devices for medical facilities, such as operating rooms and hospitals, public hygiene, or personal hygiene. In particular, the light irradiation device may be used for patient treatment purposes.

The light irradiation device according to an exemplary embodiment may be used for public treatment by applying the light irradiation device to public facilities, public use spaces, shared products, or the like, or may be used for personal treatment by applying the light irradiation device to personal facilities, personal use spaces, personal use products, and the like.

Furthermore, the light irradiation device according to an exemplary embodiment may also be added to other therapeutic devices, rather than a stand alone device.

According to an exemplary embodiment, a light irradiation device may catalyze the synthesis of functional substances in a human body, as well as being used as a light irradiation device.

Figure 10:
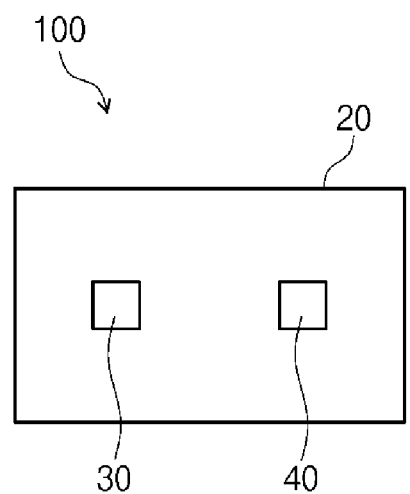
FIG. 10 is a plan view illustrating a light irradiation device according to an exemplary embodiment.
Figure 11:
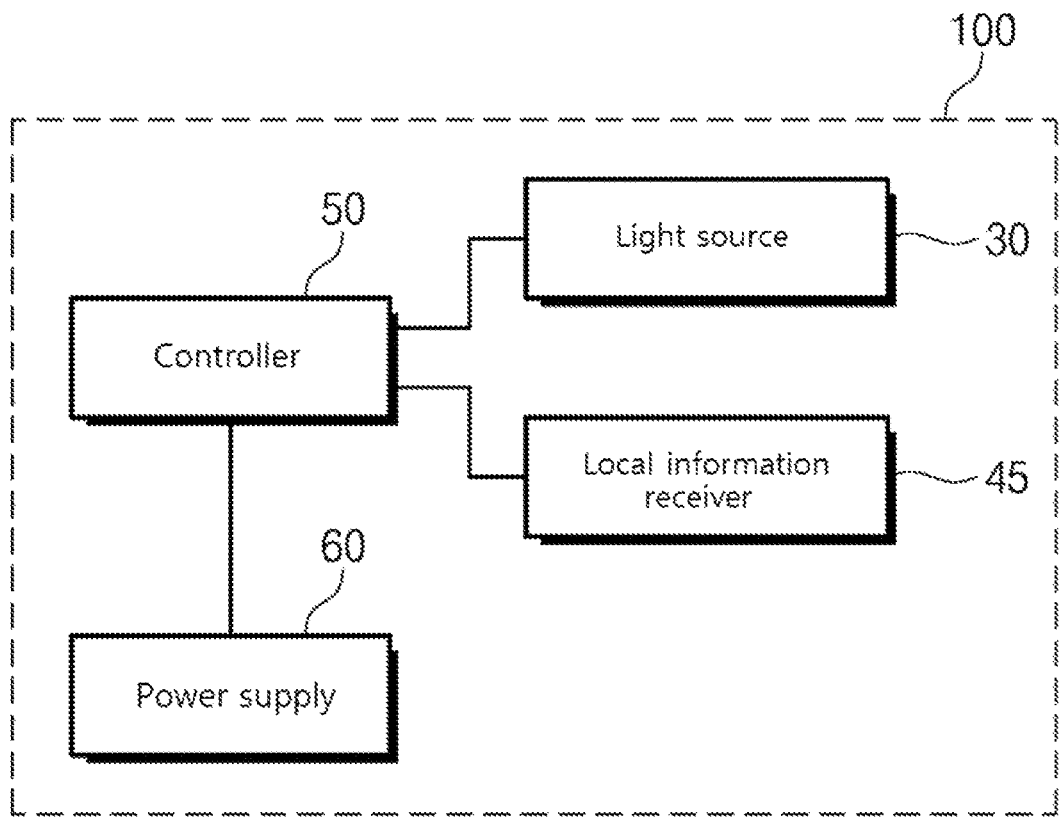
FIG. 11 is a block diagram illustrating a light irradiation device according to an exemplary embodiment.

FIG. 10 is a plan view illustrating a light irradiation device according to an exemplary embodiment, and FIG. 11 is a block diagram illustrating a light irradiation device according to an exemplary embodiment.

Referring to FIGS. 10 and 11, a light irradiation device 100 according to an exemplary embodiment includes a light source 30 for emitting light, a location information receiver 45 for receiving location information, and a controller 50 for receiving the location information from the location information receiver and controlling a dose of light emitted from the light source 30. The location information may be information that may be obtained using a global positioning system (GPS).

The light source 30 emits light of various wavelength bands, and the wavelength bands may be determined based on the purpose of the usage of the light irradiation device 100. For example, when used as an illumination device, the light irradiation device 100 according to an exemplary embodiment may emit light in a visible wavelength band. When used for wound sterilization, the light irradiation device 100 may emit light in an ultraviolet wavelength band. The wavelength band of the light source 30 based on the usage of the light irradiation device 100 will be described later.

The location information receiver 45 receives the location information from a satellite by using the GPS to calculate current location information of the light irradiation device 100. More particularly, the location information may include latitude and longitude, and the location information such as latitude and longitude of the current light irradiation device 100 may be found by the location information received from the location information receiver 45. The location information obtained using a location information signal is provided to the controller 50.

The controller 50 calculates a dose of light to be emitted by the light source 30 based on the location information provided from the location information receiver 45 to control the light source 30 to emit light having the calculated dose. In particular, the controller 50 may control whether to emit light, the amount of light, intensity of light, an emission time, and the like.

A power supply 60 is electrically connected to the controller 50, which is electrically connected to the light source 30 and the location information receiver 45, thereby supplying power to the light source 30 and the location information receiver 45. In FIG. 11, the power supply 60 is exemplarily illustrated as supplying power to the light source 30 and the location information receiver 45 through the controller 50, however, the inventive concepts are not limited thereto. In some exemplary embodiments, the light source 30 and the location information receiver 45 may be directly connected to the power supply 60, respectively.

The light source 30 and the location information receiver 45 may be disposed on a substrate 20. The substrate 20 may be a printed circuit board on which at least one of the light source 30 and the location information receiver 45 is directly mounted and a wiring or circuit is formed without being limited thereto. The substrate 20 may be sufficient as long as at least one of the light source 30 and the location information receiver 45 may be disposed thereon, and the shape or structure thereof may be not particularly limited. In some exemplary embodiments, the substrate 20 may be omitted.

The light irradiation device 100 according to an exemplary embodiment may be used for various purposes depending on the wavelength band of the light emitted from the light source 30 and a driving method.

In the light irradiation device 100 according to an exemplary embodiment, when light emitted from the light source 30 has a wavelength band similar to sunlight, the light irradiation device 100 may be used for an ordinary illumination device or a device for treating or preventing eye disease. In particular, the light irradiation device 100 may expose a user to light very similar to the sunlight, regardless of location or time.

Sunlight is irradiated differently depending on places of the earth. In general, the lower the latitude, the larger a dose of the sunlight, and the higher the latitude, the smaller a dose of the sunlight. In addition, the higher the altitude, the larger the dose of the sunlight, and the lower the altitude, the lower the dose of the sunlight. Accordingly, time or the amount of exposure to sunlight may vary depending on which country and which place the user is in.

In an exemplary embodiment, a location of the light irradiation device 100 may be detected using the location information. After a dose of sunlight at the location is calculated, a dose of a visible light corresponding to the dose of the sunlight may be emitted to the user to obtain an effect of being exposed to sunlight within a harmless degree to a human body.

This will be described in more detail with reference to the drawings.

Figure 12:
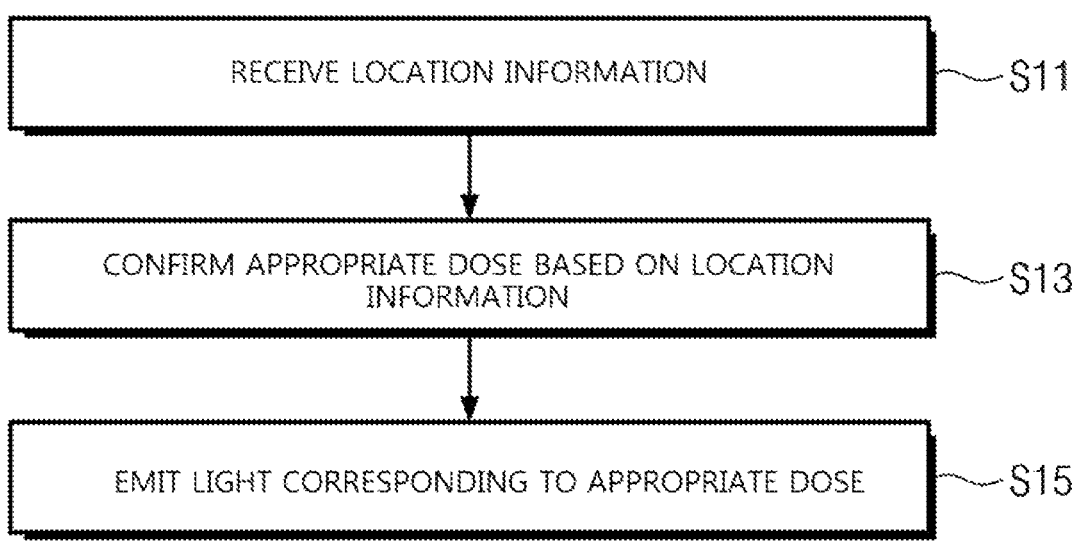
FIG. 12 is a flowchart illustrating a method of driving a light irradiation device according to an exemplary embodiment.

FIG. 12 is a flowchart illustrating a method of driving a light irradiation device according to an exemplary embodiment.

Referring to FIG. 12, the location information receiver receives the location information in S11. For example, it is determined that the light irradiation device is located in a city "B" of a country "A" based on the location information obtained from the location information receiver.

The received location information is provided to the controller, and the controller confirms or calculates an appropriate dose of light to be emitted from the light irradiation device based on the location information in S13. For example, when the city "B" of the country "A" is determined, information such as a sunrise time, a sunset time, and an average amount of sunlight of the city "B" of the country "A", as well as the latitude and longitude may be calculated. The sunrise and sunset time on the latitude and longitude may be easily checked using the latitude and longitude information, and then, the controller may determine whether it is a day or night by using an algorithm which calculates the sunrise and sunset time on the current latitude and longitude.

The controller may use information such as the sunrise time, the sunset time, and the average amount of the sunlight, and calculate a turn-on time of the light source, a turn-off time of the light source, and light intensity of the light source to allow the light source to emit light having a similar degree of actual sunlight, i.e., an appropriate dose. In particular, the controller may accurately determine day or night without an addition of an illumination sensor to properly control whether to irradiate light.

The information such as a sunrise time, a sunset time, and an average amount of sunlight at each location may be stored in a separate memory in the controller, or may be easily obtained by connecting to a separate internet network.

The controller allows the light source to turn-on or turn-off, and allows light having a dose corresponding to an appropriate dose calculated to be emitted from the light source to the user in S15. The user may be irradiated with the dose substantially the same as that of sunlight at the place where the user is, even though the user does not go outdoors.

In an exemplary embodiment, the entire wavelength bands of light emitted from the light source may be evenly mixed to have a spectrum similar to the sunlight.

The light source according to an exemplary embodiment may be similar to the sunlight, but may emit light having a wavelength band of about 380 nm to 780 nm substantially corresponding to the entire wavelength band of the visible light. As described above, a term "similar to sunlight" means that an overlapping area based on a normalized solar spectrum is more than a specific value, and a deviation of the peak from the normalized solar spectrum (e.g., a deviating degree from the peak of the normalized solar spectrum) is lower than a specific value.

The normalized solar spectrum may be represented by Equation 1 above.

Figure 13:
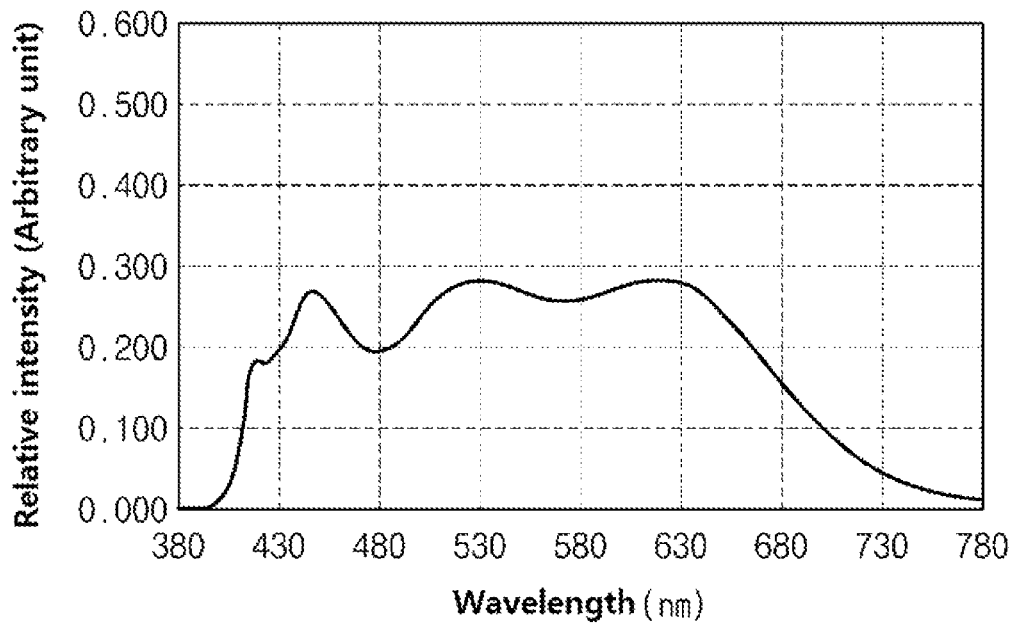
FIG. 13 is a spectrum of light emitted from a light source of in a light irradiation device according to an exemplary embodiment.

In an exemplary embodiment, a first light source may emit the light having an area that overlaps about 55% or more of an area of the normalized solar spectrum and a peak of a first light may have a deviation of about 0.14 or less from the normalized solar spectrum. For example, light emitted from the light source may be a light having a spectrum shown in FIG. 13.

According to an exemplary embodiment, even when the user is in an environment where it is difficult to be exposed to sunlight, for example, living indoors for a long time, being in a sickroom or confined space, or being active mainly at night, the user may be provided with light similar to sunlight of the place where the user is currently located at an appropriate dose for a suitable time. Accordingly, the user may be in a familiar environment and in a psychologically stable state, and controls an irradiation time by setting the sunrise or sunset time, thereby easily recovering daily biorhythm.

In addition, sunlight may be applied to a human eye to cause various therapeutic effects. For example, frequent exposure to sunlight may reduce myopia prevalence. When an outdoor activity time is not enough and not exposed to appropriate sunlight, the eye may grow long and become ellipsoidal myopia. However, according to an exemplary embodiment, this possibility may be reduced.

Furthermore, the light irradiation device according to an exemplary embodiment may provide light similar to sunlight while excluding light in a wavelength band that may be harmful to the user. For example, the light source according to an exemplary embodiment may provide light which excludes light of a wavelength band that may cause cataracts, pterygium, and keratitis, unlike the sunlight. Accordingly, when receiving sunlight outdoors for the purpose of preventing and treating myopia, there is no problem that an outdoor activity time is adjusted in consideration of time and ultraviolet values, and there is almost no risk even when exposed to light for a long time.

In the above-described exemplary embodiments, light emitted from the light source has been described as being similar to sunlight, but the inventive concepts are not limited thereto. Other lights, for example, ultraviolet or infrared lights may be applied in a similar form.

The above-described exemplary embodiments have been described as being used as a single light source instead of sunlight based on the location information, but the inventive concepts are not limited thereto. When natural light emitted from sun or light devices, i.e., an external light is present, the light source may be used as a correction light to compensate shortage of external light. For example, in places with high latitudes, an amount of sunlight may be significantly lower than in areas with low latitudes. In this case, it is necessary to compensate for the lack of sunlight. When the amount of sunlight is low, not only light in the visible light wavelength band irradiated to the user may be short, but also light in the ultraviolet light wavelength band may be insufficient. As such, the light irradiation device according to an exemplary embodiment may additionally irradiate light of the visible light wavelength band the light of the ultraviolet wavelength band, and therefore, may compensate for the insufficient light.

Figure 14:
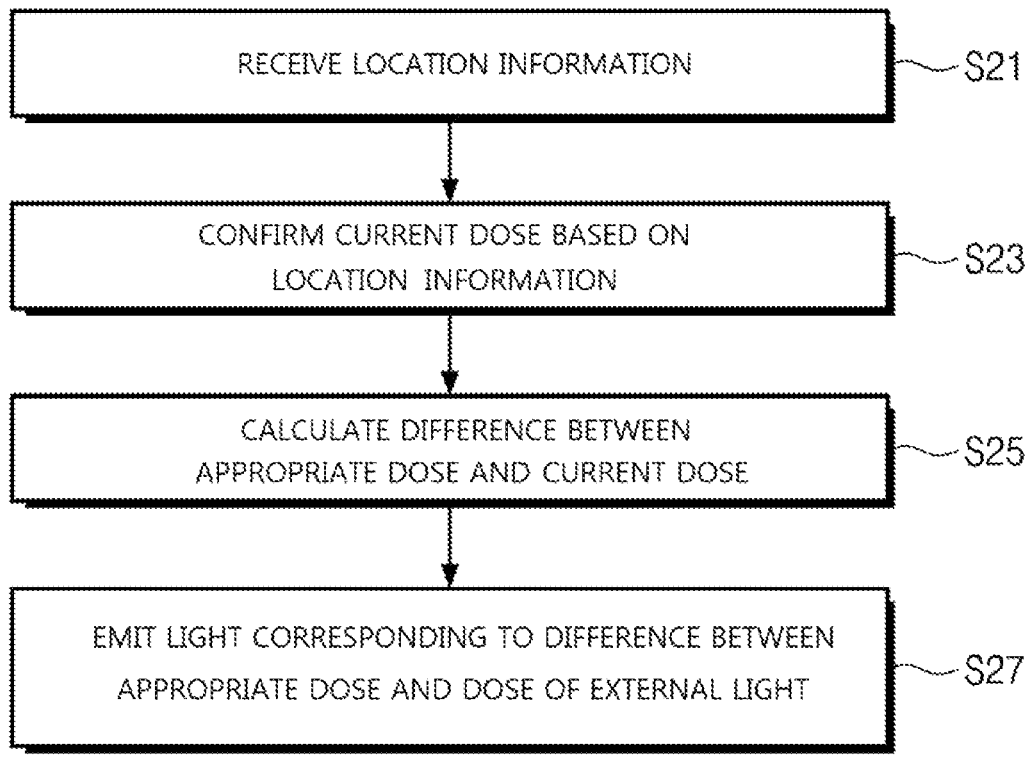
FIG. 14 is a flowchart illustrating an operation of a light irradiation device according to an exemplary embodiment.

FIG. 14 is a flowchart illustrating a method of driving a light irradiation device according to an exemplary embodiment.

Referring to FIG. 14, the location information receiver receives the location information in S21. For example, it is determined that the light irradiation device is located in a city "D" of the country "C" based on the location information obtained from the location information receiver.

The received location information is provided to the controller. The controller calculates the information such as the sunrise time, the sunset time, and the average amount of sunlight at the current location based on the location information, and calculates the current dose of actual sunlight using the information such as the sunrise time, sunset time, and average amount of sunlight in S23.

Then, a difference between the appropriate dose amount required by the user and the current dose amount is calculated in S25. For example, in the case of the "D" city of the country "C", which is located in a high latitude area and the amount of sunlight is insufficient, the amount of sunlight actually required is an appropriate dose amount and the insufficient dose is obtained by subtracting the current dose from the appropriate dose. The appropriate dose required to the user may be stored in a separate memory in the controller, or may be easily obtained by connecting to a separate internet network.

The controller allows the light source to be turn-on or turn-off and allows light having a dose corresponding to the difference between the appropriate dose and a dose of an external light, i.e., an insufficient dose, to be irradiated from the light source to a subject in S27.

The user may be irradiated with a specific light at a dose of the most appropriate degree to the user, regardless of the user's location.

In an exemplary embodiment, additional effects may be obtained by supplementing light of an insufficient specific wavelength. For example, in the case of compensating light of red to near infrared wavelength bands, immune mechanism may be activated upon wound treatment. In addition, when supplementing light of a blue wavelength band or a light of an ultraviolet wavelength band, a bactericidal effect on pathogens may be obtained.

More particularly, light in the red to near infrared wavelength bands is applied to a skin to expand blood vessels and to promote blood circulation. As such, light in the red to near infrared wavelength bands improves blood flow and promotes immune action. More specifically, red visible to near infrared lights act on the skin to be treated and stimulate intracellular mitochondria to release adenosine tri-phosphate (ATP), reactive oxygen species (ROS), and/or nitrogen oxide (NO). The ATP, ROS, and/or NO act on a wounded area to promote healing of the wound. The ATP and ROS induce expression of genes involved in an inflammatory response, which is an immune response necessary for wound healing and genes necessary for cell growth. In addition, the ROS and/or NO function to sterilize pathogens such as bacteria which penetrate the wounded area. Thus, the inflammatory response and cell growth are induced in a damaged tissue part, resulting in healing of the wound. The NO promotes migration of immune cells and increases supply of oxygen and nutrients to accelerate a process of tissue healing. The NO also expands capillaries in surrounding tissues and induces formation of new capillaries. Light in the red to near infrared wavelength bands may correspond to light in a wavelength band of about 610 nm to about 940 nm. In an exemplary embodiment, light in the red to near infrared wavelength bands may be light in a red visible wavelength band, e.g., about 610 nm to about 750 nm, or in an infrared wavelength band, e.g., about 750 nm to about 940 nm. Alternatively, light of the red to near infrared wavelength bands may be about light of 830 nm, light of 850 nm, or light of 890 nm in the infrared wavelength band.

Light in the blue wavelength band acts on photosensitizers present in pathogens such as bacteria, microbes, fungi, and the like to induce death of pathogens by damaging cells. Light in the blue wavelength band corresponds to an absorption wavelength of porphyrin, i.e., the photosensitizer present in microbes. Light in the blue wavelength band exhibits high bactericidal power, particularly at wavelengths of 400 nm to 420 nm, and 455 nm to 470 nm, which corresponds to the absorption wavelength band of the porphyrin, which is the photosensitizer. The porphyrin is a pigment which is essential element for the intracellular oxygen transfer process. The porphyrin exhibits high absorption, particularly at wavelengths from about 402 nm to about 420 nm, and also absorbs wavelengths from about 455 nm to 470 nm. In an exemplary embodiment, porphyrin contents vary depending on types of bacteria. As such, wavelength and intensity of light in the blue wavelength band may be adjusted to be used for the purpose of killing a specific bacterium. When light in the blue wavelength band is applied to the bacteria, the porphyrin in the bacteria absorbs light in the blue wavelength band, and a reactive oxygen species is generated in cells of the bacteria by energy of light in the blue wavelength band. The reactive oxygen species accumulates in the cells of the bacteria, oxidizes cell walls of the bacteria, and therefore the bacteria are killed. Light in the blue wavelength band may correspond to light in a wavelength band of about 400 nm to about 500 nm. In an exemplary embodiment, light in the blue wavelength band may be light in a wavelength band of about 400 nm to about 420 nm. More particularly, light of the blue wavelength band may be light having a wavelength of 405 nm.

Light of the ultraviolet wavelength band is effective in killing pathogens such as bacteria, microbes, fungi, and the like. When the ultraviolet light is applied to the bacteria, DNA in the bacteria absorbs the ultraviolet light and its DNA structure may be changed by energy of the ultraviolet light. Because bases constituting the DNA, such as purine and pyrimidine, absorb the ultraviolet light strongly, binding of thymine and adenine in the DNA is broken by the absorption of light, and therefore, thymine dimer is formed as a result of light absorption. This process leads to modification of the DNA, which leads to death of the bacteria because the modified DNA is incapable of cell proliferation. The DNA may absorb light in a wavelength range of about 240 nm to about 280 nm. Accordingly, when the ultraviolet light is used as a supplementary light in addition to the natural light, the ultraviolet light may be a light in a wavelength band of about 100 nm to about 400 nm, and may be UVA, UVB, or UVC. UVA. The UVA may have a wavelength band of about 315 nm to about 400 nm, the UVB may have a wavelength band of about 280 nm to about 315 nm, and the UVC may have a wavelength band of about 100 nm to about 280 nm. In an exemplary embodiment, the ultraviolet light may correspond to the UVC, and may have a wavelength band of about 240 nm to about 280 nm. More particularly, the ultraviolet light may be light having a wavelength of 275 nm.

Light of the ultraviolet wavelength band may promote the synthesis of vitamin D in the human body. In particular, the UVB has an effect of promoting synthesis of vitamin D. The ultraviolet light applied to the human body may be in the ultraviolet B wavelength band. When the human body is exposed to the ultraviolet B wavelength band, 7-dehydrocholesterol in the skin cells synthesizes cholecalciferol (i.e., Vitamin D3).

In an exemplary embodiment, upon ultraviolet irradiation, the amount of light may be variously changed, and a total dose to a target to be sterilized is set within a range harmless to the human body. In addition, within a range for promoting the synthesis of vitamin D, the amount of ultraviolet light is set to a dose in a harmless range so as not to cause a light burn.

In particular, a dose of ultraviolet light that may not cause harm to the human body per day is called an "allowable dose". The light source may emit the ultraviolet light within the allowable dose. For example, the allowable dose of the ultraviolet light may be about 30 mJ/m2 to about 1,000,000 mJ/m2, or may be about 30 mJ/m2 to about 10000 mJ/m2, and the dose may be changed depending on the wavelength band.

Table 1 shows time taken to a sunburn depending on a solar zenith angle, a dose of UVB causing the sunburn, a dose of UVB required to synthesize vitamin D 1000IU. Here, the dose of UVB was measured based on face and hands (10%) of skin type I-II.

TABLE 1

| Solar Zenith Angle (°) | Time for sunburn (min) | UV Dose to Sunburn (UVB ; J/m$^2$) | UV Dose to Vit.D 1000 IU(UVB; J/m$^2$) |
| --- | --- | --- | --- |
| 70 | 180 | $2.5 \times 10^4$ | $2.8 \times 10^4$ |
| 63 | 120 | $1.7 \times 10^4$ | $1.1 \times 10^4$ |
| 57 | 60 | $8.3 \times 10^3$ | $5.9 \times 10^3$ |
| 53 | 45 | $6.2 \times 10^3$ | $4.1 \times 10^3$ |
| 50 | 36 | $5.0 \times 10^3$ | $3.2 \times 10^3$ |
| 47 | 30 | $4.1 \times 10^3$ | $2.6 \times 10^3$ |

TABLE 1-continued

| Solar Zenith Angle (°) | Time for sunburn (min) | UV Dose to Sunburn (UVB ; J/m$^2$) | UV Dose to Vit.D 1000 IU(UVB; J/m$^2$) |
|---|---|---|---|
| 42 | 26 | 3.6 × 10$^3$ | 2.1 × 10$^3$ |
| 38 | 22 | 3.0 × 10$^3$ | 1.8 × 10$^3$ |
| 36 | 20 | 2.8 × 10$^3$ | 1.5 × 10$^3$ |
| 32 | 18 | 2.5 × 10$^3$ | 1.4 × 10$^3$ |
| 24 | 15 | 2.1 × 10$^3$ | 1.1 × 10$^3$ |
| 0 | 12 | 1.7 × 10$^3$ | 0.9 × 10$^3$ |

As seen in Table 1, ultraviolet rays are irradiated at different values depending on the altitude of the sun, and a dose leading to the sunburn is also different. This means that the dose of ultraviolet rays of the irradiated sunlight is different from each other depending on places on the earth, and the doses leading to the sunburn caused by the sunlight are also different. Accordingly, it may be confirmed that the dose required for the user in the place and a maximum allowable dose need to be set for each place through location setting based on the location information. In an exemplary embodiment, the controller may tabulate the information, store the tabulated information in a memory, or access the information through internet, thereby controlling the amount of light emitted from the light source.

As such, in the light irradiation device according to an exemplary embodiment, the light source is controlled depending on the timing or location, and then light corresponding to the sunlight or light whose dose is appropriately corrected as necessary may be provided to the human body.

The above-described driving method of the light irradiation device may be changed in various forms according to the wavelength band of the light source. Hereinafter, various exemplary embodiments according to type and wavelength band of the light source will be described.

In an exemplary embodiment, a plurality of light sources may be provided. Here, the plurality of light sources may emit light of different wavelength bands from one another. The plurality of light sources may be driven at the same time or independently.

Figure 15A:
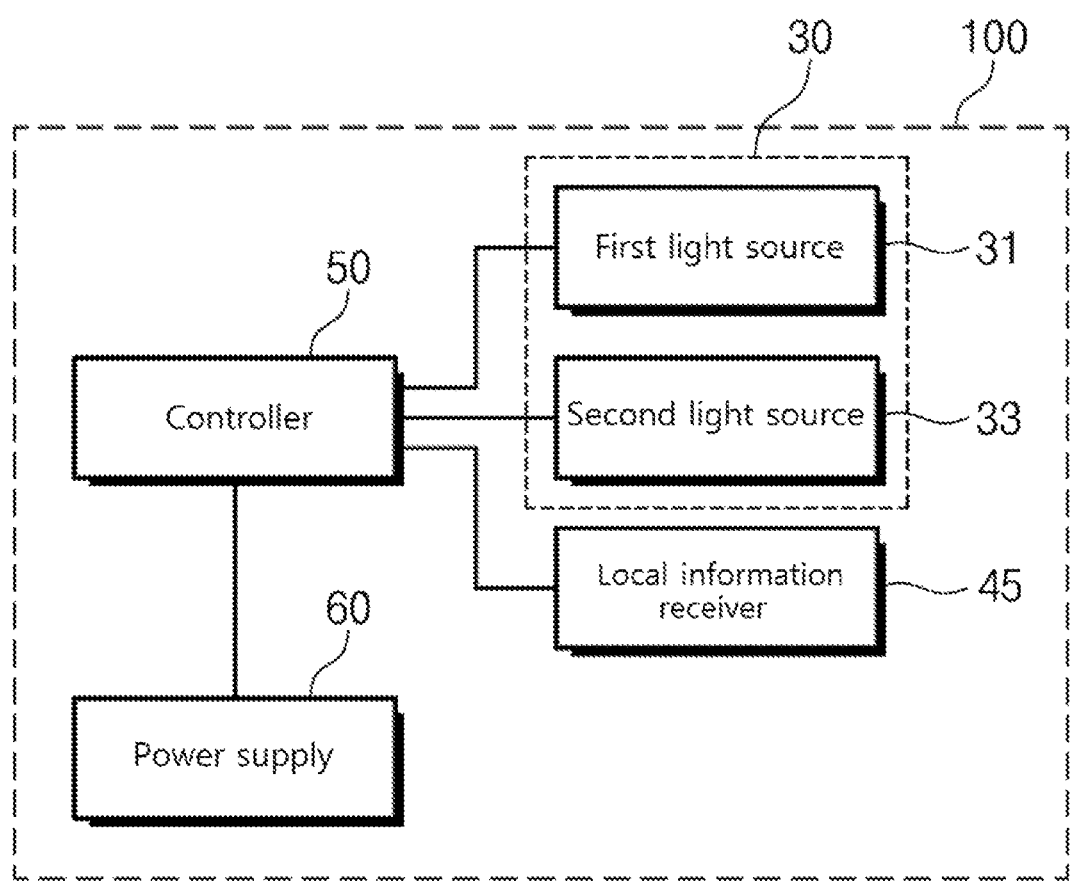
FIG. 15A is a block diagram of a light source including a first light source and a second light source according to an exemplary embodiment.
Figure 15B:
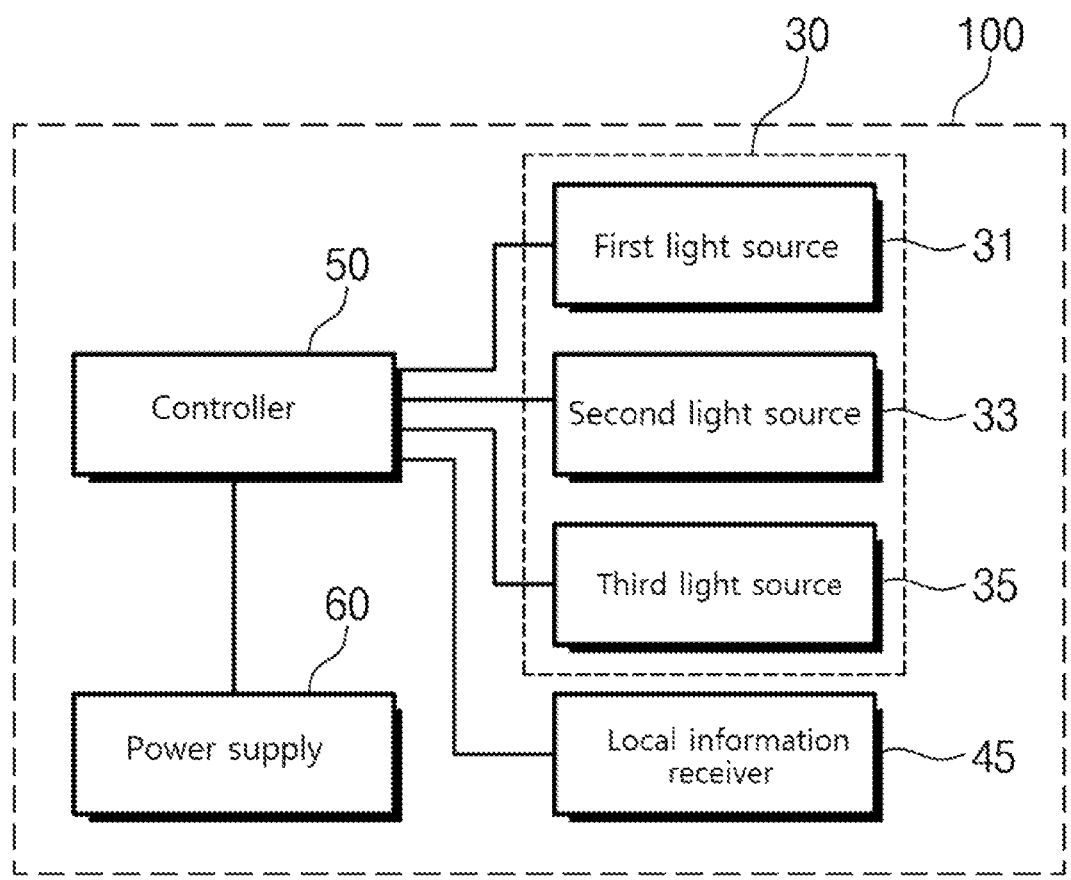
FIG. 15B is a block diagram of a light source including a first light source, a second light source, and a third light source according to another exemplary embodiment.

FIG. 15A illustrates a light source including a first light source and a second light source in a light irradiation device according to an exemplary embodiment, and FIG. 15B illustrates a light source including a first light source, a second light source, and a third light source. FIGS. 15A and 15B exemplarily illustrate that two and three light sources are provided, but the inventive concepts are not limited thereto. The light source may be provided in a different number from the above in other exemplary embodiments.

Referring to FIG. 15A, the light source may include a first light source 31 emitting light of a first wavelength band and a second light source 33 emitting light of a second wavelength band different from the first wavelength band.

In an exemplary embodiment, the first light source 31 may emit light in a wavelength band similar to that of sunlight as described above, that is, light including an ultraviolet light, a visible light, and an infrared light. The second light source 33 may emit light in an ultraviolet wavelength band.

In an exemplary embodiment, the first light source 31 may emit light in the visible light wavelength band and the second light source 33 may emit light in the ultraviolet wavelength band.

In an exemplary embodiment, the first light source 31 may emit light of the blue wavelength band and the second light source 33 may emit light of the ultraviolet wavelength band.

In an exemplary embodiment, the first light source 31 may emit light in the visible light wavelength band and the second light source 33 may emit light in the infrared wavelength band. Alternatively, the second light source 33 may emit light in the red to near infrared wavelength bands.

In an exemplary embodiment, the first light source 31 may emit light of the blue wavelength band and the second light source 33 may emit light of the infrared wavelength band. Alternatively, the second light source 33 may emit light in the red to near infrared wavelength bands.

In an exemplary embodiment, the first light source 31 may emit light in the ultraviolet wavelength band and the second light source 33 may emit light in the near infrared wavelength band. Alternatively, the second light source 33 may emit light in the red to near infrared wavelength bands.

Referring to FIG. 15B, the light source 100 may include a first light source 31 emitting light of a first wavelength band, a second light source 33 emitting light of a second wavelength band different from the first wavelength band, and a third light source 35 emitting light of a third wavelength band different from the first and second wavelength bands. The first to third light sources 31, 33, and 35 may be driven independently from one another, and thus, the first to third light sources 31, 33, and 35 may be combined in various forms. In this case, the controller 50 may provide each light individually, or may mix at least two lights of first to third lights to irradiate the user.

In an exemplary embodiment, the first light source 31 may emit light in the ultraviolet wavelength band, the second light source 33 may emit light in the visible light wavelength band, and the third light source 35 may emit an infrared wavelength band.

In the light irradiation device 100 according to an exemplary embodiment, the amount and intensity of light emitted from the light source 31 may be set in a plurality of various modes. The user may select any one of the various modes, and thus, light may be applied depending on the mode.

For example, when the light irradiation device includes the first to third light sources 31, 33, and 35, the light irradiation device 100 may control the light source in various forms and manners. A first mode is a mode for turning-on only the first light source 31, a second mode is a mode for turning-on the first and second light sources 31 and 33, a third mode is a mode for turning-on the first and third light sources 31 and 35, and a fourth mode is a mode for blinking on and off the first light and turning-on the third light.

These modes may be set automatically but may also be set manually by the user. In this manner, a set value of the light irradiation device may be easily changed depending on a condition desired by the user.

The light irradiation device according to an exemplary embodiment may be variously applied where illumination and light treatment are required. For example, the light irradiation device may be used not only for illumination devices in general places, but also for medical facilities, such as operating rooms and hospitals, and for public health or personal care. In particular, the light irradiation device according to an exemplary embodiment may be used for patient treatment.

In particular, the light irradiation device may be used for public treatment purposes by being employed in public facilities, public use spaces, and public use products, or may be used for personal treatment purposes by being employed in personal facilities, personal use spaces, and personal use products. The light irradiation device may also be used in addition to other treatment devices, rather than being used exclusively for light irradiation devices.

According to exemplary embodiments, the light irradiation device is capable of obtaining a variety of light irradiation effects in the harmless range to the human body.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A light irradiation device comprising:
a first light source substrate and a second light source substrate spaced apart from each other, each of the first and second light source substrates including at least one of:
a first light source configured to emit first light in a visible wavelength band; and
a second light source configured to emit second light, in which at least part of a wavelength band of the second light source is different from the wavelength band of the first light source, to catalyze synthesis of a functional substance comprising vitamin D in a target irradiated with the second light;
a driving unit configured to control a light emission direction of each of the first and second light source substrates, respectively;
a first tilt member directly disposed on the first light source substrate and configured to adjust an angle at which the first light source substrate is inclined; and
a second tilt member directly disposed on the second light source substrate and configured to adjust an angle at which the second light source substrate is inclined,
wherein:
the second light includes light in a wavelength band of ultraviolet B;
an area of a spectrum of the wavelength band of the first light overlaps 55% or more of an area of a solar spectrum normalized in a range, in which a color temperature is 2600 K to 7000 K; and
a peak of the first light in a wavelength range of 380 nm to 490 nm has a deviation of 0.14 or less from the normalized solar spectrum.

2. The light irradiation device of claim 1, wherein the second light includes light in a wavelength band of 280 nm to 315 nm.

3. The light irradiation device of claim 1, wherein the second light further includes light in a wavelength band of ultraviolet A and light in a wavelength band of ultraviolet C.

4. The light irradiation device of claim 3, wherein the second light source is configured to emit the second light to the target in a predetermined dose.

5. The light irradiation device of claim 4, wherein the predetermined dose of the second light is in a range of 30 J/m² to 10000 J/m².

6. The light irradiation device of claim 4, wherein:
the predetermined dose of the second light is configured to vary depending on a timing of a day or a year; and
an amount of light emitted from the second light source is configured to be controlled depending on the predetermined dose.

7. The light irradiation device of claim 4, wherein:
the predetermined dose of the second light is configured to vary depending on a location of a human body; and
an amount of light emitted from the second light source is configured to be controlled depending on the predetermined dose.

8. The light irradiation device of claim 1, wherein the wavelength band of the first light source is in a range of 380 nm to 780 nm.

9. The light irradiation device of claim 8, wherein the normalized solar spectrum is expressed by following Equation 1;

$$E(\lambda, T) = \frac{2hc^2}{\lambda^5} \cdot \frac{1}{e^{hc/\lambda kT} - 1} \quad \text{Equation 1}$$

λ: wavelength (μm)
h: Planck's constant
c: Speed of light
T: Absolute temperature
k: Boltzmann constant.

10. The light irradiation device of claim 1, further comprising a sensing sensor configured to sense a human body.

11. The light irradiation device of claim 10, further comprising a controller configured to control an on/off of each of the first and second light sources depending on whether the human body is present.

12. The light irradiation device of claim 11, wherein:
the sensing sensor is configured to sense a movement of the human body; and
the driving unit is configured to change the light emission direction of each of the first light source substrate and second light source substrate depending on whether the human body has moved.

13. The light irradiation device of claim 12, wherein the on/off of at least one of the first light source and second light sources is configured to be controlled by a user.

14. The light irradiation device of claim 12, wherein the on/off of at least one of the first light source and second light sources is configured to be controlled depending on a predetermined program.

15. The light irradiation device of claim 12, further comprising:
a location information receiver configured to receive location information,
wherein the controller is configured to receive the location information from the location information receiver and to control a dose of light emitted from the first and second light sources,
wherein the controller is configured to calculate the dose of light to be emitted from the first and second light sources based on the location information, and to control the first and second light sources to emit light of the calculated dose.

16. The light irradiation device of claim 15, wherein the location information receiver is configured to:
calculate the location information of the light irradiation device;
calculate a dose of an external light of a place where the light irradiation device is located based on the location information; and
control the first and second light sources to emit light corresponding to a difference between the calculated dose and the dose of the external light.

17. The light irradiation device of claim 1, wherein the first light in a wavelength range of 680 nm to 780 nm has a deviation greater than 0.14 from the normalized solar spectrum.

18. A light irradiation device comprising:
a first light source substrate and a second light source substrate spaced apart from each other, each of the first and second light source substrates including at least one of:
   a first light source configured to emit first light in a visible wavelength band; and
   a second light source configured to emit second light having a wavelength band of ultraviolet B to catalyze synthesis of a functional substance comprising vitamin D to a target irradiated with the second light;
a driving unit configured to control a light emission direction of each of the first and second light source substrates, respectively;
a first tilt member directly disposed on the first light source substrate and configured to adjust an angle at which the first light source substrate is inclined; and
a second tilt member directly disposed on the second light source substrate and configured to adjust an angle at which the second light source substrate is inclined,
wherein:
the wavelength band of the first light source is in a range of 380 nm to 780 nm;
an area of a spectrum of the wavelength band of the first light overlaps 55% or more of an area of a solar spectrum normalized in a range, in which a color temperature is 2600 K to 7000 K; and
a peak of the first light in a wavelength range of 380 nm to 490 nm has a deviation of 0.14 or less from the normalized solar spectrum.

19. The light irradiation device of claim 18, further comprising:
   a location information receiver configured to receive location information; and
   a controller configured to receive the location information from the location information receiver and control a dose of light emitted from the first and second light sources,
wherein the controller is configured to calculate the dose of light to be emitted from the first and second light sources based on the location information and control the first and second light sources to emit light of the calculated dose.

20. The light irradiation device of claim 19, wherein the location information receiver is configured to:
   calculate the location information of the light irradiation device;
   calculate a dose of an external light of a place where the light irradiation device is located based on the location information; and
   control the first and second light sources to emit light corresponding to a difference between the calculated dose and the dose of the external light.

* * * * *